United States Patent
Walker

(10) Patent No.: US 9,186,241 B2
(45) Date of Patent: Nov. 17, 2015

(54) GRAFT FIXATION DEVICE

(71) Applicant: Peter Michael Sutherland Walker, Bellevue Hill (AU)

(72) Inventor: Peter Michael Sutherland Walker, Bellevue Hill (AU)

(*) Notice: Subject to any disclaimer, the term of this patent is extended or adjusted under 35 U.S.C. 154(b) by 0 days.

(21) Appl. No.: 13/921,208

(22) Filed: Jun. 19, 2013

(65) Prior Publication Data
US 2014/0094912 A1    Apr. 3, 2014

(30) Foreign Application Priority Data
Jun. 22, 2012    (AU) ................. 2012902627

(51) Int. Cl.
*A61F 2/08*    (2006.01)
*A61B 17/04*    (2006.01)

(52) U.S. Cl.
CPC .......... *A61F 2/0811* (2013.01); *A61B 17/0401* (2013.01); *A61B 2017/0414* (2013.01); *A61B 2017/0417* (2013.01); *A61F 2002/0852* (2013.01); *A61F 2002/0882* (2013.01)

(58) Field of Classification Search
CPC ............................... A61F 2/0811; A61F 17/04
USPC ............................. 623/13.11–13.15
See application file for complete search history.

(56) References Cited

U.S. PATENT DOCUMENTS

| | | | |
|---|---|---|---|
| 5,306,301 A | 4/1994 | Graf et al. | |
| 5,464,427 A * | 11/1995 | Curtis et al. | 606/232 |
| 6,117,161 A * | 9/2000 | Li et al. | 606/232 |
| 8,388,655 B2 * | 3/2013 | Fallin et al. | 606/232 |
| 8,512,378 B2 * | 8/2013 | Green et al. | 606/232 |
| 8,777,992 B2 * | 7/2014 | Yeung et al. | 606/232 |
| 2004/0087953 A1 | 5/2004 | Singhatat et al. | |
| 2006/0190041 A1 | 8/2006 | Fallin et al. | |
| 2007/0270857 A1 | 11/2007 | Lombardo et al. | |
| 2012/0065731 A1 * | 3/2012 | Justin et al. | 623/13.14 |
| 2013/0085503 A1 * | 4/2013 | Smith et al. | 606/96 |
| 2013/0304120 A1 * | 11/2013 | Stone et al. | 606/232 |
| 2014/0172095 A1 * | 6/2014 | Graf et al. | 623/13.14 |
| 2014/0214163 A1 * | 7/2014 | Demmer et al. | 623/13.14 |
| 2014/0243978 A1 * | 8/2014 | Beck et al. | 623/13.14 |

FOREIGN PATENT DOCUMENTS

| | | |
|---|---|---|
| EP | 2623066 A1 | 7/2013 |
| WO | WO9720522 | 6/1997 |
| WO | WO02091959 A1 | 11/2002 |
| WO | WO2007109665 A8 | 9/2007 |

* cited by examiner

*Primary Examiner* — Suzette J Gherbi
(74) *Attorney, Agent, or Firm* — Clayton, Howarth & Cannon, P.C.

(57) ABSTRACT

A fixation device and method for retaining a graft. The device including: an elongate body having a first end and a second end; a transverse passage for retaining a graft retainer element; a first aperture located in the first end, and a second aperture in the second end; the first aperture and second aperture defining respective ends of a longitudinal through path. The method using the fixation device for drawing a graft through a first tunnel defined in a first bone and reining the graft when through.

24 Claims, 18 Drawing Sheets

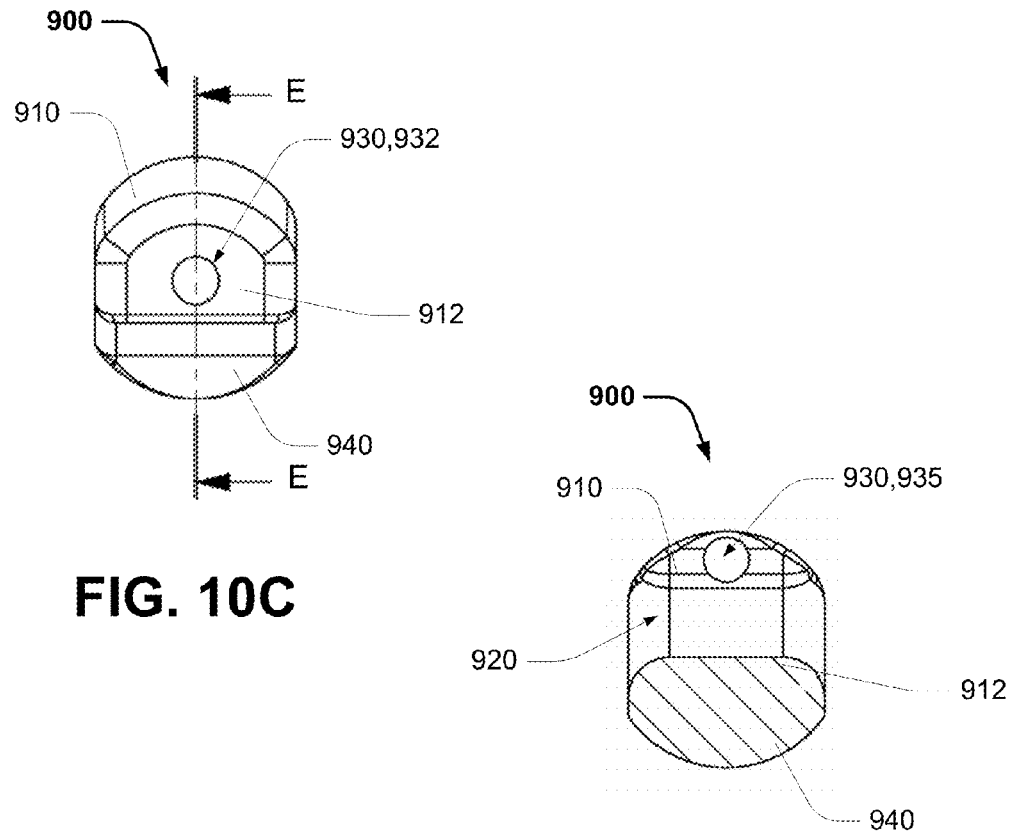
FIG. 10C
FIG. 10D
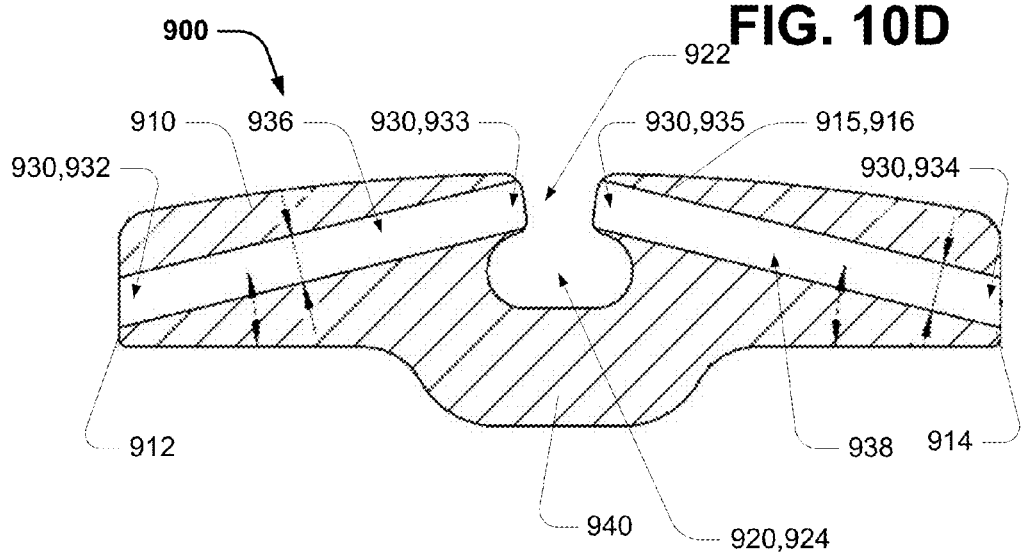
FIG. 10E

GRAFT FIXATION DEVICE

FIELD OF THE INVENTION

The present invention relates to retaining and fixation devices and in particular to devices for retaining or fastening grafts.

The invention has been developed primarily for use as a fixation device that can be used to retain or fasten a graft (including tendon or ligament) with respect to a bone and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

The present disclosure will be used with reference to an anterior cruciate ligament ("ACL") reconstruction, but it will be understood that the technology and methods of the present invention may have other applications for reconstruction of other parts of body The ACL reconstruction can be performed in numerous ways. All common methods involve drilling holes or tunnels in the femur and tibia. These can be drilled using a variety of techniques. Grafts such as autografts, allografts or artificial biomaterials may be used to extend between the femoral tunnel and the tibial tunnel. The graft is then fixed to the appropriate bone structure, again numerous techniques being suitable. The replacement graft is fixed to the femur and tibia, most commonly by a screw into the adjacent bone, it being understood that staples, pins and similar devices may also be used.

A known device for retaining a graft proximal to the aperture to a femoral tunnel is an EndoButton™, as described in: U.S. Pat. No. 6,533,802 (issued 18 Mar. 2003). Similar devices are taught in U.S. Pat. No. 5,645,588 (issued 8 Jul. 1997) and U.S. Pat. No. 5,306,301 (issued 26 Apr. 1994).

The EndoButton™ includes an integrally formed continuous ring of polyester tape for fixation of soft tissue. The EndoButton can be drawn through the femoral tunnel through manipulation of a pair of suture loops each taken about and through one of respective pair of through apertures located at the ends of the device. When the device exits the through the femoral tunnel the pair of suture loops are manipulated to lay the device flat across the aperture to the femoral tunnel. Use of the EndoButton requires both pairs of suture loops to be manipulated and appropriately tensioned.

OBJECT OF THE INVENTION

It is an object of the present invention to overcome or ameliorate at least one of the disadvantages of the prior art, or to provide a useful alternative.

It is an object of the invention in its preferred form to provide a graft fixation device for retaining graft located with a bone tunnel.

SUMMARY OF THE INVENTION

According to an aspect of the invention there is provided a graft fixation device comprising:
an elongate body having a first end and a second end;
a transverse passage for retaining a graft retainer element;
a first aperture located in the first end, and a second aperture in the second end; the first aperture and second aperture defining respective ends of a longitudinal through passage.

Preferably, the body has a lower protruding portion located below the transverse passage. More preferably, the lower protruding portion is a smooth bulged portion that extends at least the longitudinal span of the transverse passage.

Preferably, the transverse passage is defined as a channel being open to an upper surface of the device. More preferably, a lower portion of the channel extends toward the first end. Most preferably, the channel has an hook or 'L' shaped profile. Alternatively, transverse through passage can be symmetric in profile.

Alternatively, the transverse through passage can be defined by a closed through aperture (being asymmetric or symmetric).

Preferably, the body tapers-down toward the second end; More preferably, the body tapers down toward the first end. Most preferably, the body tapers down from a central region toward both the first end and second end.

Preferably, the graft retainer element is a closed loop element adapted to be located in the transverse passage for retaining the graft with respect to the device. More preferably, the loop is a continuous woven material. Alternatively, the loop is integrally formed with an artificial graft.

Preferably, the first aperture and the second aperture is located proximal to the centre of the respective first end and second end. Preferably, the longitudinal through passage is sized to receive a length of suture.

Preferably, the longitudinal through passage extends from the first aperture to a first intermediate aperture proximal to the transverse passage, and from a second intermediate aperture proximal to the transverse passage to the second aperture. More preferably, the longitudinal through passage is intersected by the transverse passage. Most preferably, the longitudinal through passage is defined by a first passage segment and a second passage segment, each passage segment being substantially straight inwardly-upwardly through-passages extending from a respective first end and second end. Alternatively, the longitudinal through passage can be axially directed.

According to an aspect of the invention there is provided a method of using a fixation device for drawing a graft through a first tunnel defined in a first bone, the method comprising the steps of:
(a) providing a fixation device;
(b) coupling the fixation device to a loop having a stop abutting a first end of the fixation device;
(c) coupling the fixation device to a first end of the graft;
(d) applying tension to a leading length of the loop to cause the fixation device to draw the graft up through the tunnel;
(e) applying tension to a leading length of the loop to cause the fixation device to exit the tunnel;
(f) applying tension to the leading edge and a trailing length of the loop to cause the fixation device to rotate flat across the tunnel; and
(g) applying tension to the trailing length of the loop to thereby extract the loop from the fixation device.

According to an aspect of the invention there is provided a method of using a fixation device for drawing a graft through a first tunnel defined in a first bone, the method comprising the steps of:
(a) providing a fixation device;
(b) coupling the fixation device to a length of suture having a stop abutting a first end of the fixation device;

(c) coupling the fixation device to a first end of the graft;
(d) applying tension to a leading portion of the length of suture to cause the fixation device to draw the graft up through the tunnel;
(e) applying tension to a leading portion of the length of suture to cause the fixation device to exit the tunnel;
(f) applying tension to the leading edge and a trailing portion of the length of suture to cause the fixation device to rotate flat across the tunnel; and
(g) applying tension to the trailing portion of the length of suture to thereby extract the length of suture from the fixation device.

Preferably, the device is used during knee surgery when replacing a tendon or ligament.

Preferably, the graft is a ligament or tendon being either a transplant or artificial.

BRIEF DESCRIPTION OF THE DRAWINGS

A preferred embodiment of the invention will now be described, by way of example only, with reference to the accompanying drawings in which:

FIG. 10C is an end view of the device of FIG. 9;
FIG. 10D is a sectional end view of the device taken along line D-D of FIG. 10A;
and
FIG. 10E is a sectional side view of the device taken along line E-E of FIG. 10C.

PREFERRED EMBODIMENT OF THE INVENTION

Figure 1:
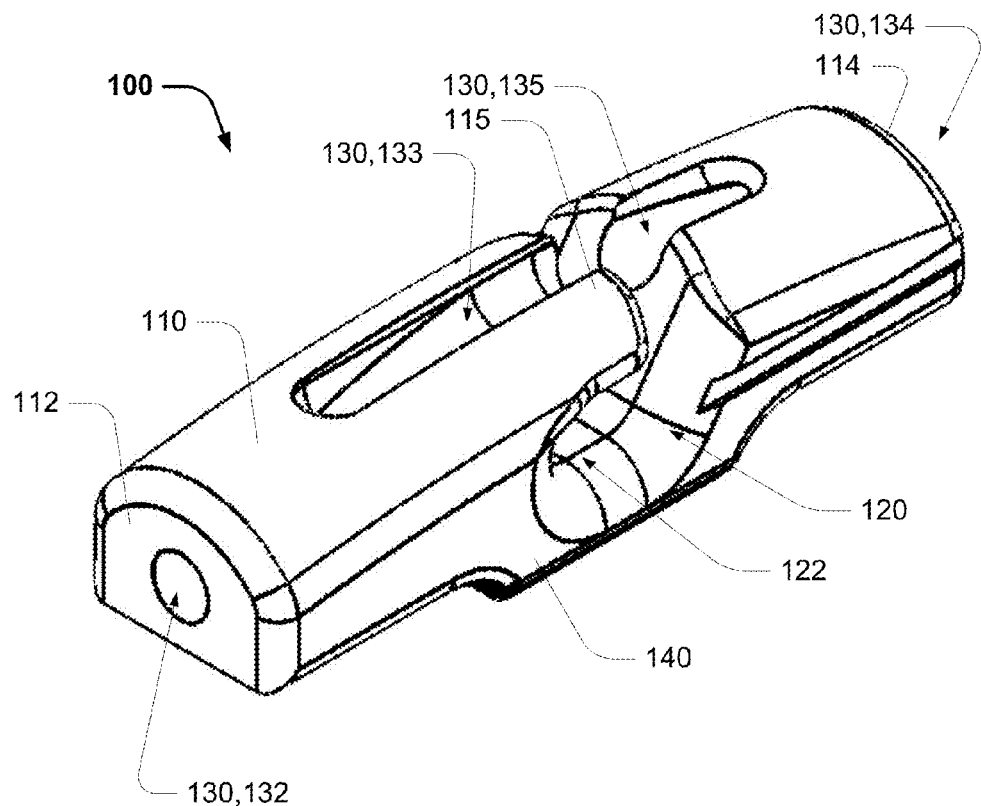
FIG. 1 is a perspective view of an embodiment fixation device according to the invention.

Referring initially to FIG. 1 of the drawings, and FIG. 2A to FIG. 2E, an embodiment fixation device 100, by way of example only, can comprise:
an elongate body 110 having a first end 112 and a second end 114;
a transverse passage 120 for retaining a graft retainer element (not shown);
a longitudinal through passage 130 having a first aperture 132 located in the first end, and a second aperture 134 in the second end.

The first aperture 132 and second aperture 134 define respective ends of the transverse passage 130. The longitudinal through passage is typically sized to receive a length of suture. Typically, the first aperture and the second aperture can be located proximal to the centre of the respective first end and second end.

Figure 2A:
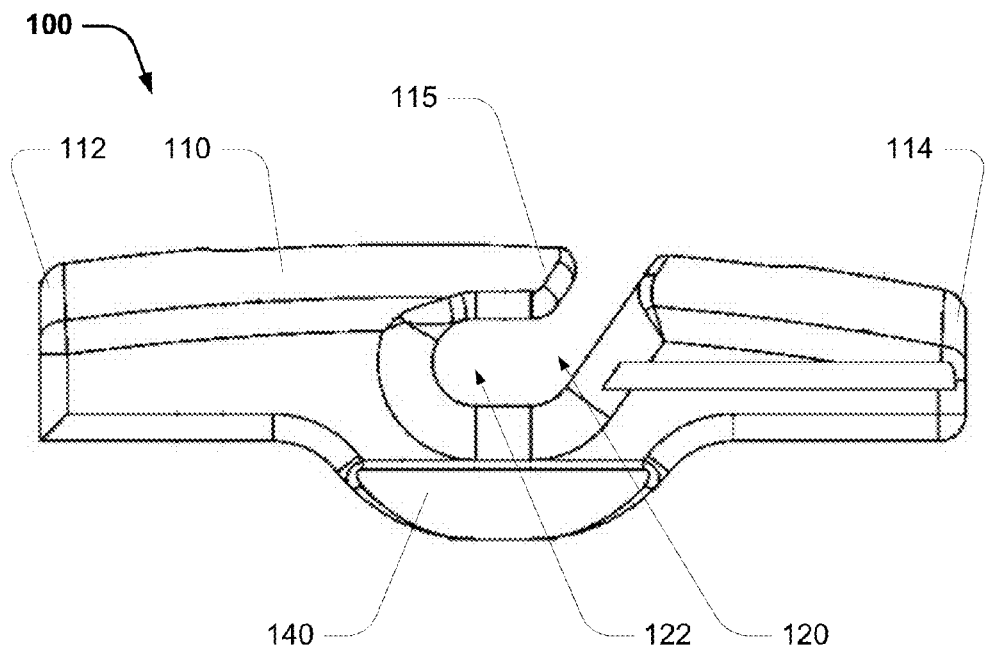
FIG. 2A is a side view of the device of FIG. 1.
Figure 2B:
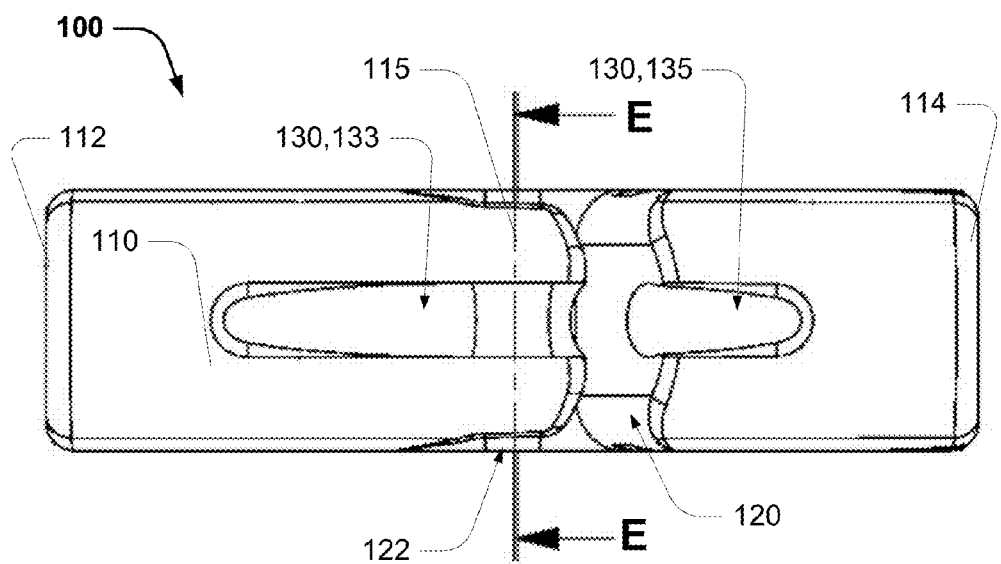
FIG. 2B is a plan view of the device of FIG. 1.
Figure 2C:
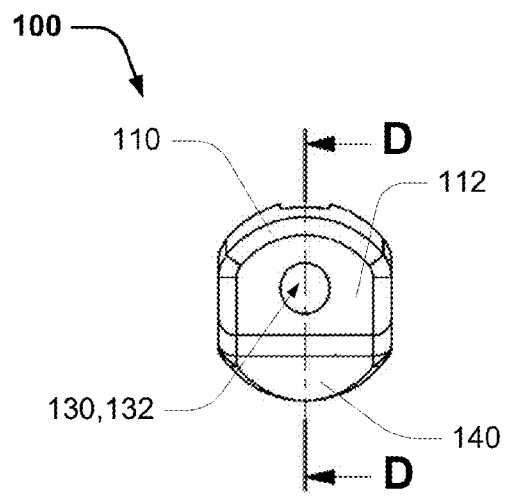
FIG. 2C is an end view of the device of FIG. 1.
Figure 2D:
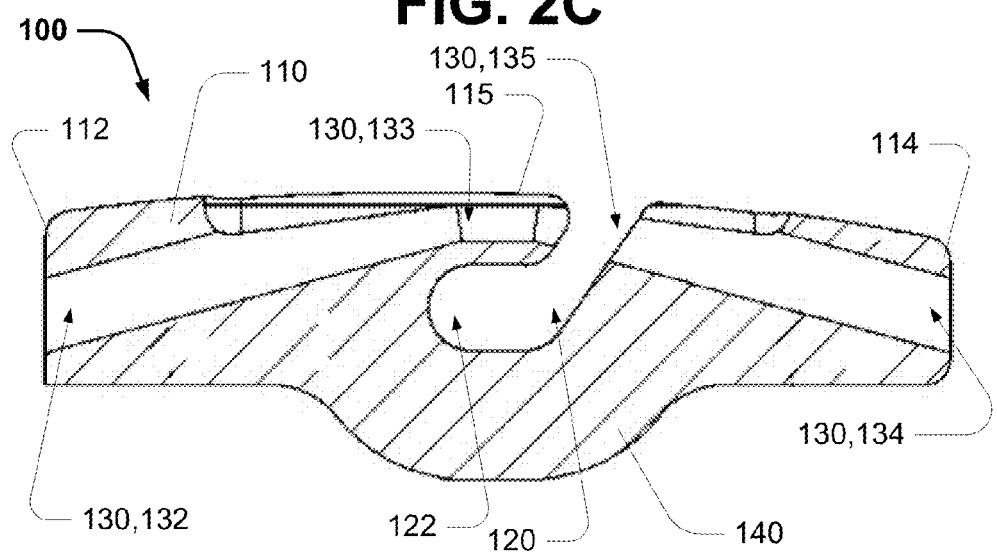
FIG. 2D is a sectional side view of the device taken along line D-D of FIG. 2C.
Figure 2E:
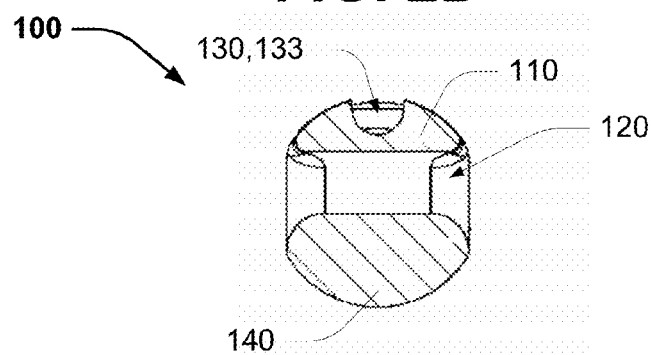
FIG. 2E is a sectional end view of the device taken along line E-E of FIG. 2B.
Figure 3A:
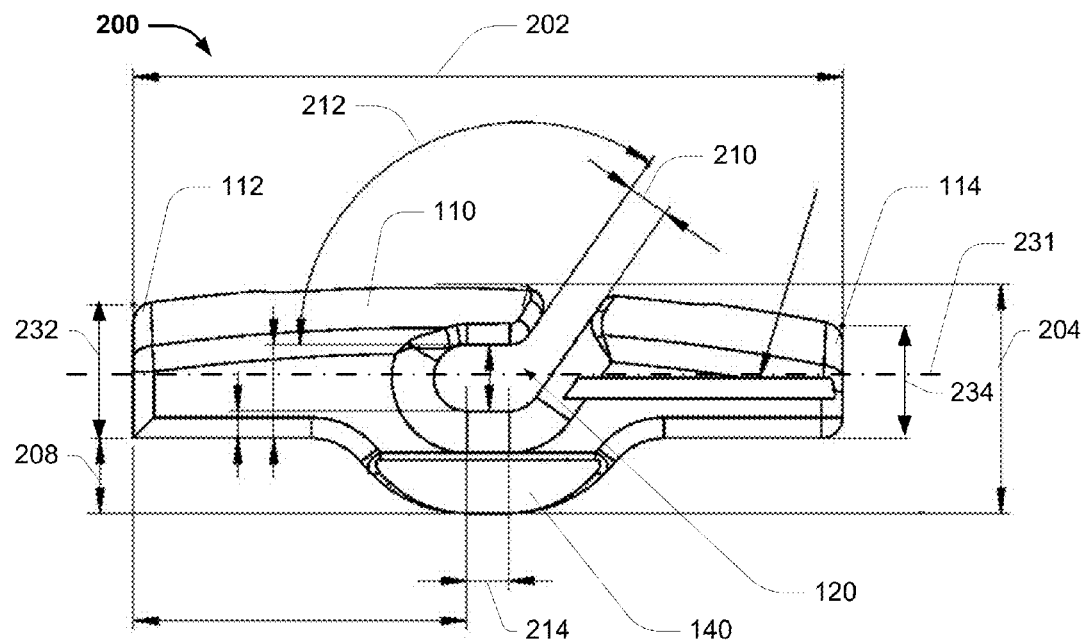
FIG. 3A is a side view of an embodiment fixation device according to the invention.
Figure 3B:
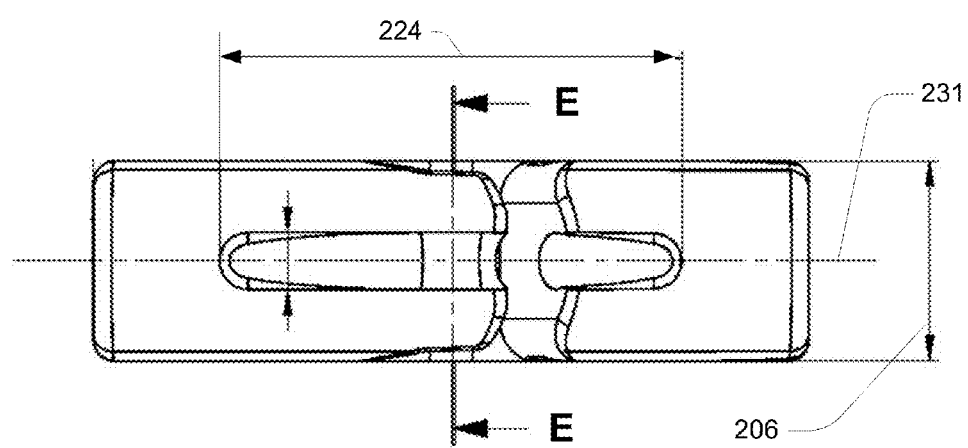
FIG. 3B is a plan view of the device of FIG. 3A.
Figure 3C:
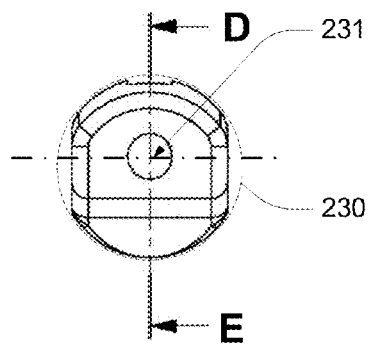
FIG. 3C is an end view of the device of FIG. 3A.
Figure 3D:
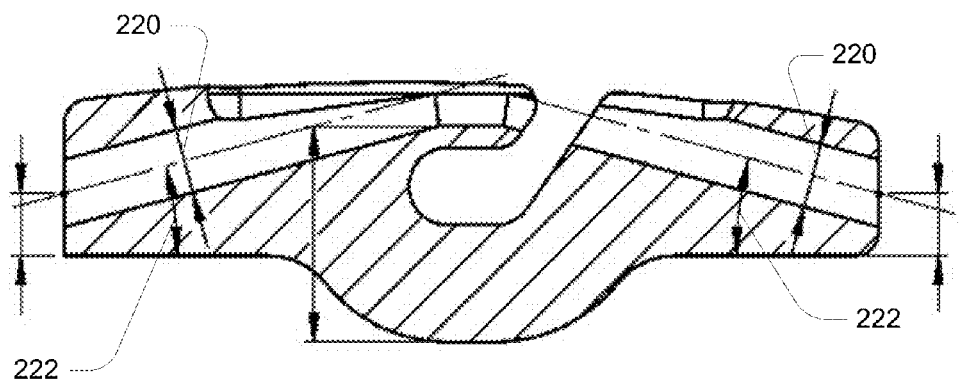
FIG. 3D is a sectional side view of the device taken along line D-D of FIG. 3C.
Figure 3E:
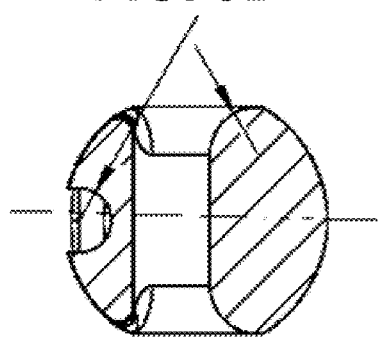
FIG. 3E is a sectional end view of the device taken along line E-E of FIG. 3B.

By way of example only, the longitudinal through passage 130 extends from the first aperture 132 to a first intermediate aperture 133 proximal to the transverse passage, and from a second intermediate aperture 135 proximal to the transverse passage to the second aperture 134. In this embodiment, the longitudinal through passage is intersected by the transverse passage. As best shown in FIG. 2D, the longitudinal through passage 130 is defined by a first passage segment 136 and a second passage segment 138, wherein the first passage segment is a substantially straight inwardly-upwardly through-passage extending from the first end 112, and wherein the second passage segment is a substantially straight inwardly-upwardly through-passage extending from the second end 114. It will be appreciated that, the longitudinal through passage can be defined in a plurality of configurations wherein the passage comprises a first aperture 132 and a second aperture 134 defined proximal to respective ends of the device. For example, in an embodiment, the longitudinal through passage can be axially directed.

In this embodiment, the body has a lower protruding portion 140 located below the transverse passage 120. The lower protruding portion is defined by a smooth bulged portion that extends at least the longitudinal span of the transverse passage. It will be appreciated that the protuberance can provide longitudinal rigidity across the transverse passage, and can assist in locating the device about the tibial through passage.

In accordance with the present example embodiment, the transverse passage 120 can be defined as a channel that is open to an upper surface of the device. The lower portion of the channel can extend (referring to reference 122) toward the first end. It will be appreciated that, by way of example only, the channel can be an angled slot, or have a hook or 'L' shaped profile. Alternatively, a transverse through passage can be defined a closed through aperture—wherein a graft retainer element is manufactured in situ with the device. An open channel can be necked down to resist release of an inserted graft retainer element.

The body tapers down from a central region 115 toward both the first end 112 and second end 114. This can assist movement of the device through a bone tunnel.

The graft retainer element is typically, but not limited to, a closed loop element adapted to be located within the transverse passage. By way of example, the graft retainer element can be a loop of continuous woven material.

The graft retainer element can be used for retaining the graft with respect to the device, or alternatively can be a loop that is integrally formed with an artificial graft. It will be appreciated that, by having an open channel, a closed loop can be located after manufacture of the device. Alternatively, the loop can be manufactured in situ (or integrally formed with) the device.

By way of example, a graft retainer element can be a loop of fibre material (for example suture material), which can be placed over (or through) the transverse passage. The graft can then be retained by passing it through the loop.

It will be appreciated that the device can be used during knee surgery for fixation of a graft, wherein the graft can include a ligament or tendon being either a transplant or artificial. All references to a graft includes a transplant or artificial tendon and/or ligament.

By way of example an artificial graft can be combined from multiple artificial tendon strands that are braided to form a graft retainer element in situ.

It is noted that edges of the device have been rounded to avoid sharp edges, for example: about the exterior of the device; and about or within the passages.

In an embodiment, by way of an example only, a fixation device 200 can have dimensions as defined with reference to FIG. 3A through FIG. 3E.

Accordingly, referring to FIG. 3A through FIG. 3E, a fixation device 200 can have:
- an overall length 202 of about 20 mm;
- an overall height 204 of about 5.5 mm;
- an overall width 206 of about 5.5 mm;
- a lower protruding portion height 208 of about 1.8 mm;
- a transverse passage having a slot width 210 of about 1 mm an inclination 212 of about 125 degrees; a lower portion of the passage extends 214 about 1 mm having a height 216 of about 1.6 mm, having a concave terminus having a radius 218 of about 0.8 mm;
- a longitudinal through passage having nominal bore diameter 220 of about 1.35 mm, a first passage segment and a second passage segment each inclined 222 at about 15 degrees; an intermediate open segment of the passage extending 224 about 1 mm; and
- the body has an overall diameter 230, about the longitudinal axis 231, of io about 5.5 mm; and the body tapers down from a central toward both the first end having a height 332 of about 3.2 mm and second end having a height 234 of about 2.7 mm.

Depending on the size of the device (thereby imparting a structural strength) and the intended use of the device, it will be appreciated that the device can be manufactured from materials including (but not limited to) any one or more of the materials selected from the set comprising: metals (such a titanium), metal alloys (such as stainless steels, cobalt-chromium alloys, and titanium alloys), metal composites, ceramics, polymers or plastics (such as polyethylene) and carbon fibre.

FIG. 4A through FIG. 4E show an embodiment fixation device 100 configured for retaining a graft.

In this configuration, a length of suture material 310 is threaded through the device to define a loop having a trailing length 312 and a leading length 314. The suture material loop having a stop 316 which abuts the first end 112 of the fixation device. In this embodiment, the stop 316 is a knot formed at an intermediate position of the suture material 310. It will be appreciated that the stop can be associated with the suture material 310, including any one of the following methods selected from the set: applied to, integrally formed with, interconnected with, or attached to.

In this configuration a graft retainer element 320 is located within (and retained by) the transverse passage 120. The graft retainer element is by way of example only a loop graft retainer element. By way of example, a graft 330 can be passed through the loop graft retainer element and doubled back—as shown in FIG. 4C.

Figure 4A:
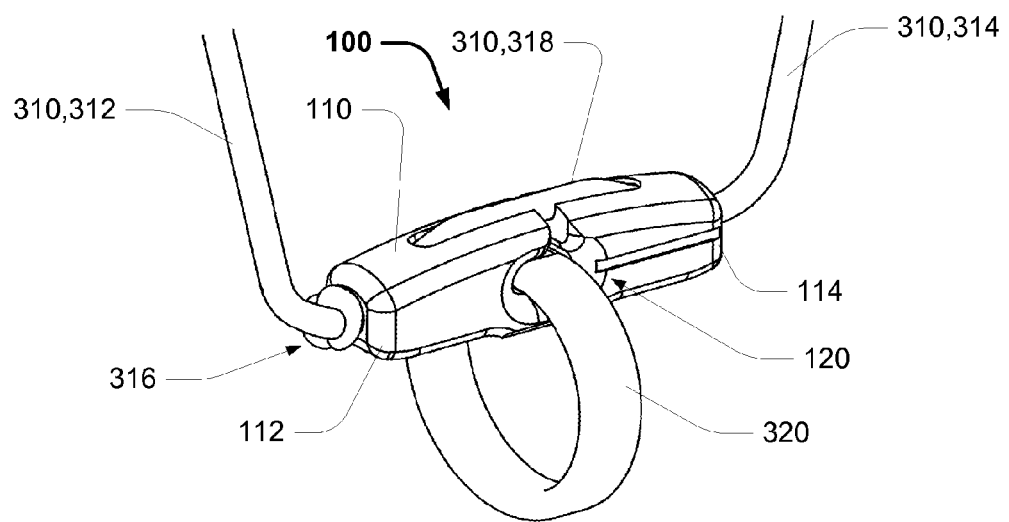
FIG. 4A is a perspective view of an embodiment fixation device according to the invention, shown configured with a suture loop and a graft fixation loop.
Figure 4B:
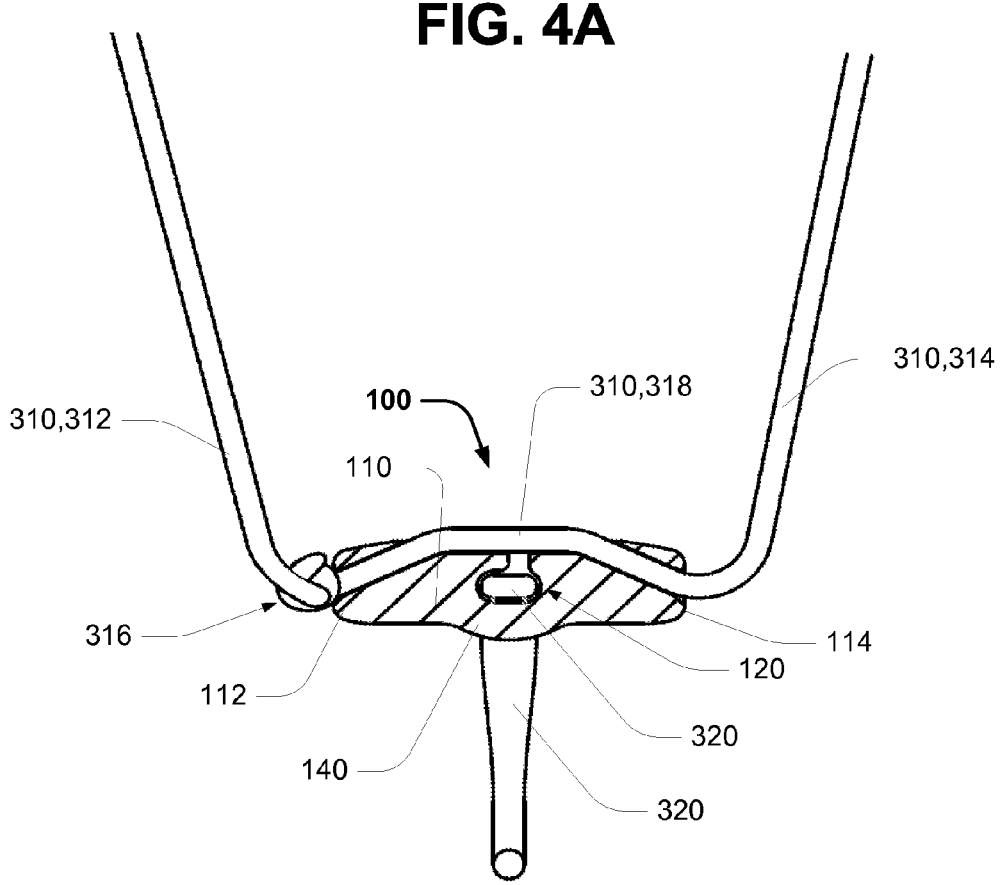
FIG. 4B is a sectional side view of the device of FIG. 4A.
Figure 4C:
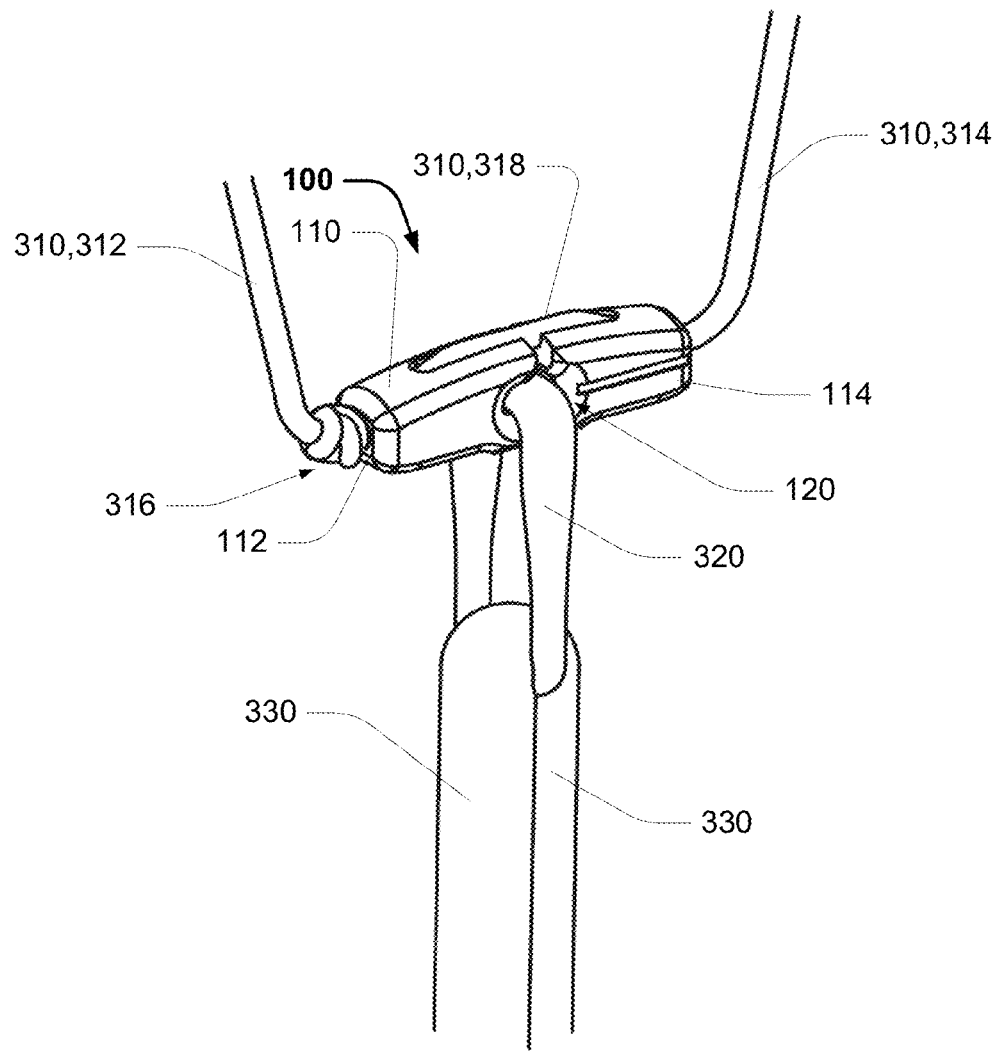
FIG. 4C is a perspective view of the device of FIG. 4A, shown with a joined graft.

It will be appreciated that a portion 318 of the length of suture material 310, extends across the transverse passage 120 and over the graft retainer element 320—as shown in FIG. 4B. This reduces the risk that the graft retainer element 320 can be dislodged, particularly while tension is maintained on the leading length 314.

Figure 4D:
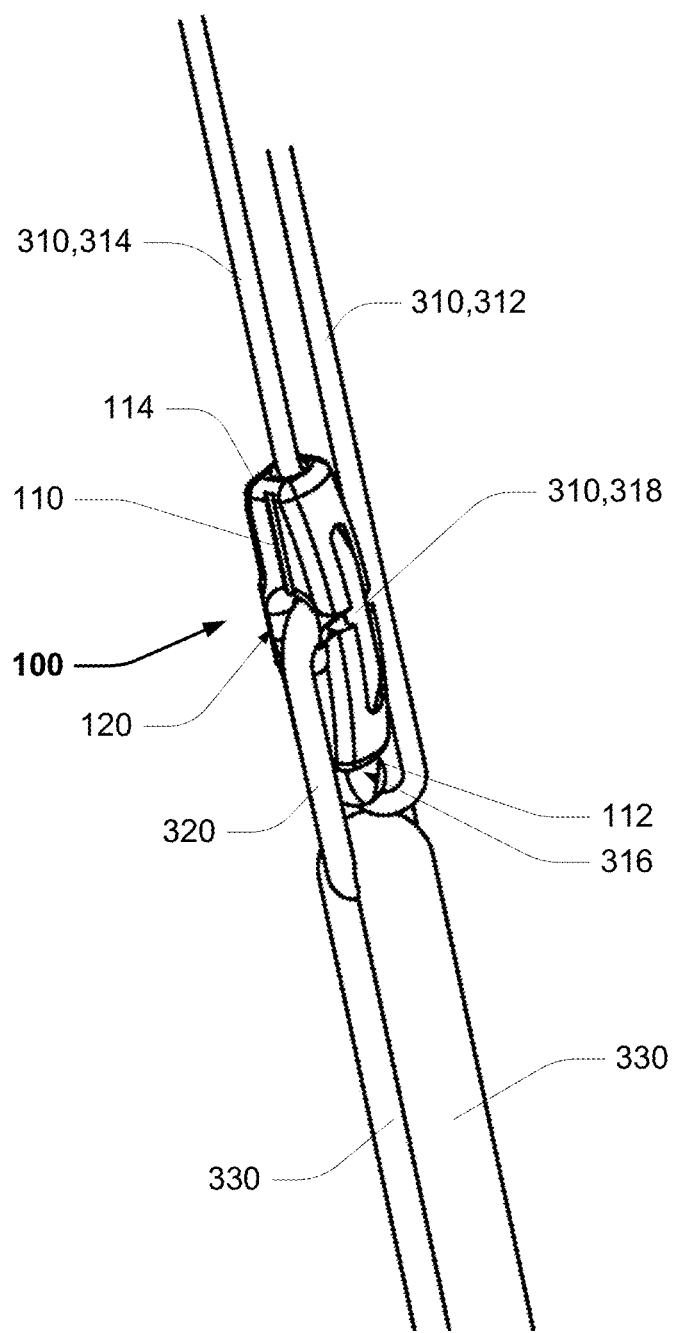
FIG. 4D is a perspective view of the device of FIG. 4C, shown in a configuration for drawing through a femoral tunnel.
Figure 4E:
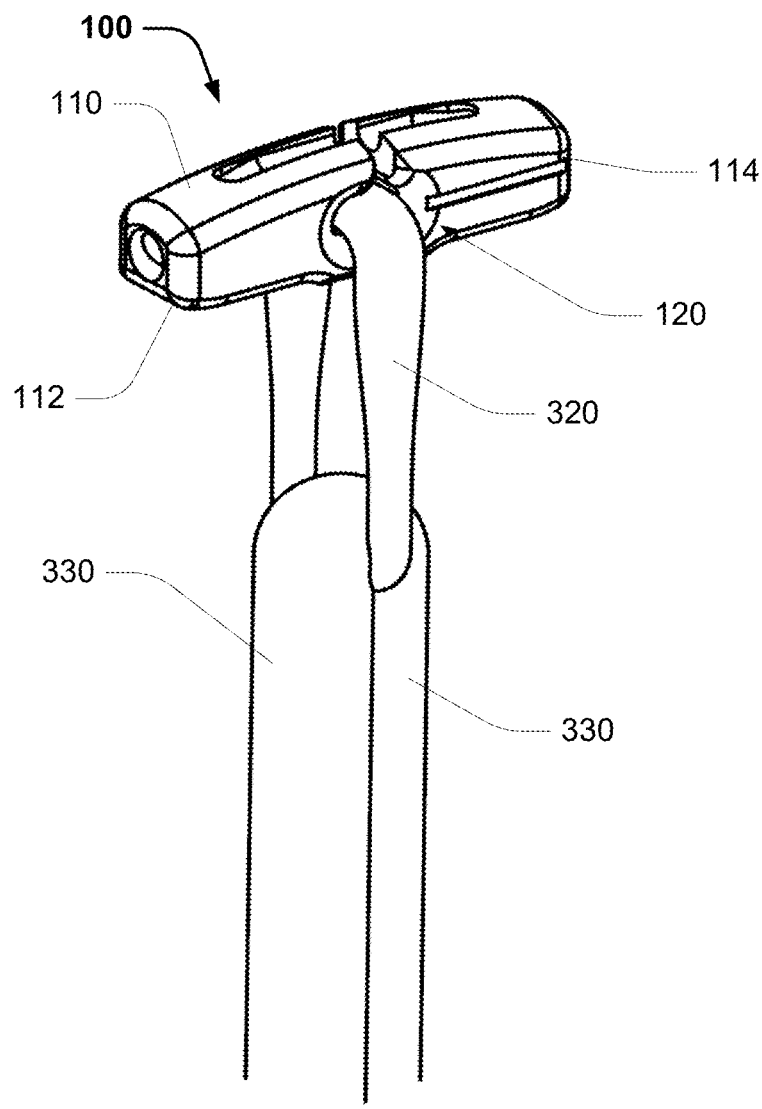
FIG. 4E is a perspective view of the device of FIG. 4C, shown with the suture loop removed.

In use, by applying tension to a leading length 314 of the suture loop 310, the fixation device 100 can be drawn end on in the direction of the leading edge—as shown in FIG. 4D. By applying tension to the trailing length 314 of the suture loop 310, the device can be rotated flat, and the suture loop can be extracted from the device—as shown in FIG. 4E.

FIG. 5A through FIG. 5F show method steps for using an embodiment fixation device (for example fixation device 100) configured for retaining a graft during an anterior cruciate ligament ("ACL") reconstruction.

FIG. 5A through FIG. 5F shows the femur 510 and tibia 520 are first drilled to form a femoral tunnel 512 and tibial tunnel 522 respectively. In this example, it is noted that the femoral tunnel 512 and tibial tunnel 522 can have a single diameter (typically about 7-10 mm in diameter) throughout their respective length.

Upon providing a fixation device 100; a first end of the graft 330 is coupled to the fixation device, for example using a graft retainer element 320; and a loop (for example a loop of suture material 310) is coupling the fixation device 100, wherein a stop 316 on the loop abutting a first end of the fixation device.

Figure 5A:
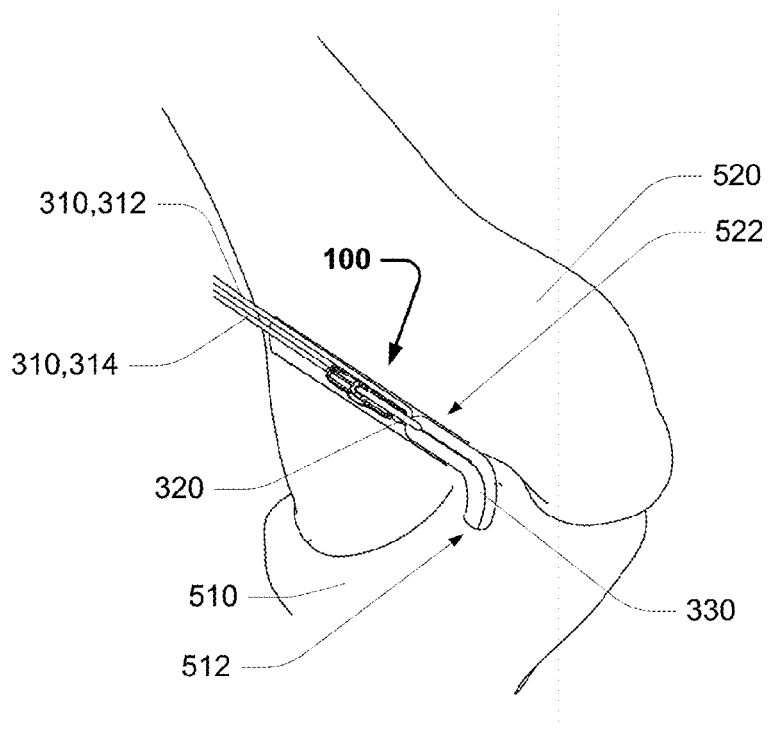
FIG. 5A-5F are perspective views illustrating steps involved in utilisation of the invention in conjunction with an ACL reconstruction.

FIG. 5A shows tension applied to a leading length 314 of the loop causes the fixation device to draw the graft up through the tunnel.

Figure 5B:
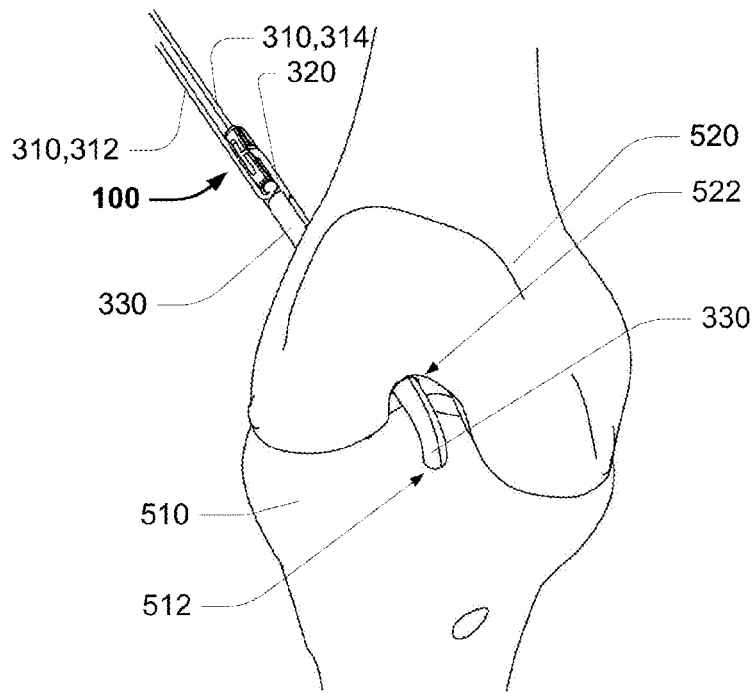

FIG. 5B shows tension applied to a leading length 314 of the loop to cause the fixation device to exit the tunnel 522.

Figure 5C:
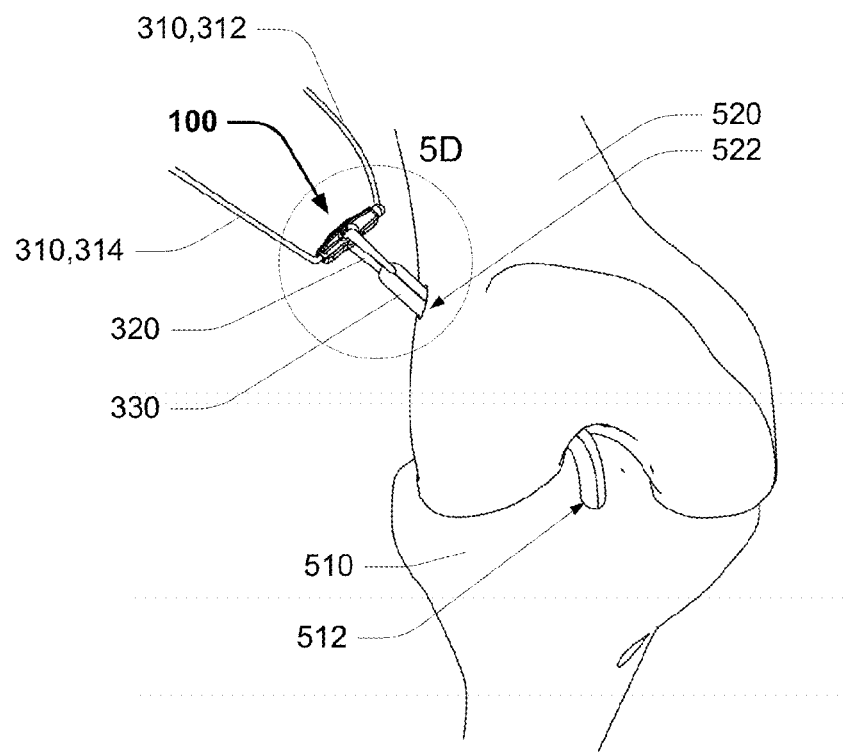
Figure 5D:
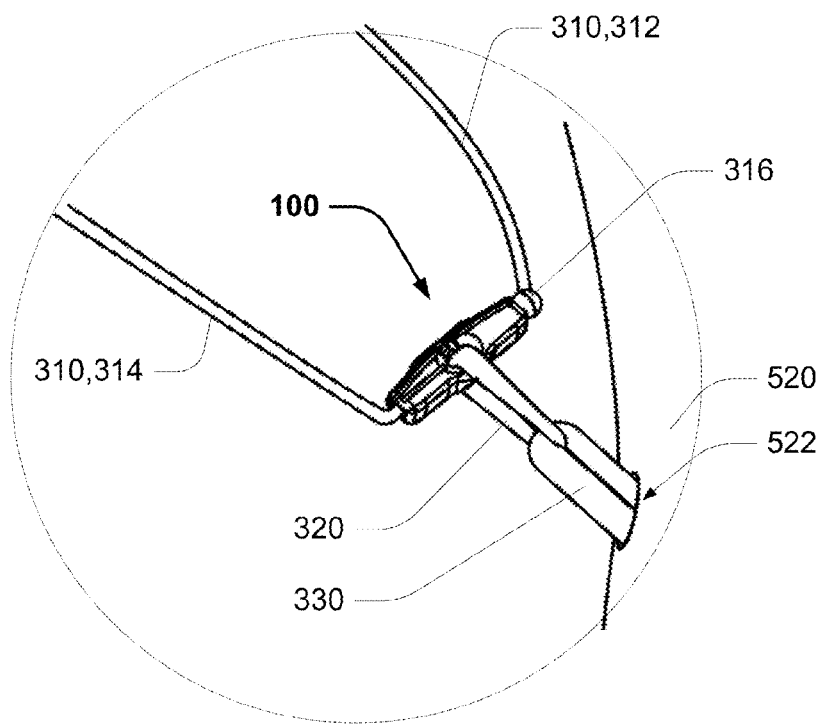
Figure 5E:
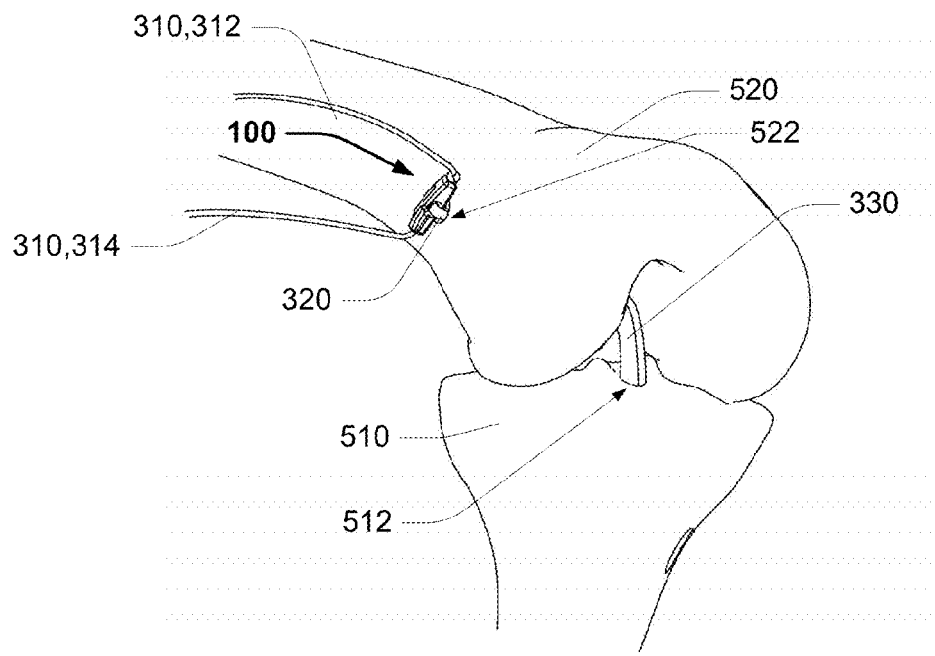

FIG. 5C, FIG. 5D and FIG. 5E shows that, by applying tension to the leading edge 314 and a trailing length 312 of the loop, the fixation device 100 is rotated flat across the tunnel 522.

Figure 5F:
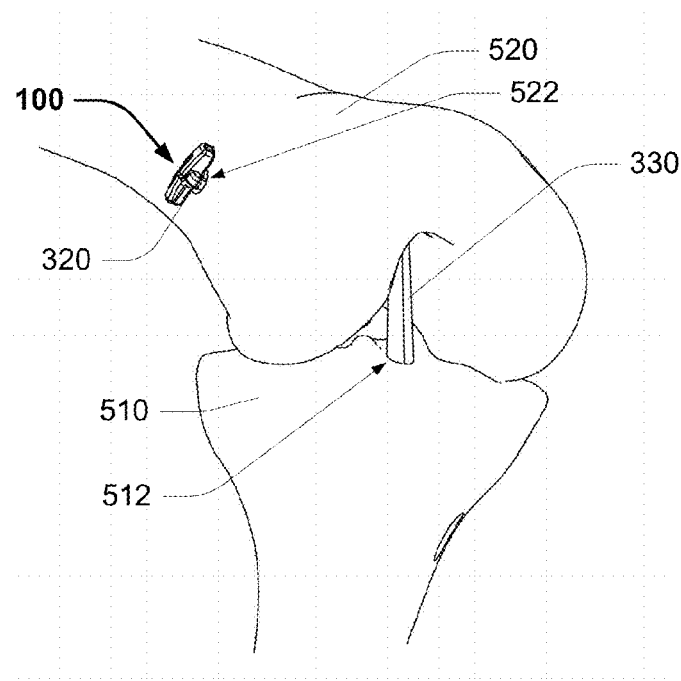

FIG. 5F shows that by applying tension to the trailing length 312 of the loop enables extraction of the loop 310 from the fixation device 100, leaving the fixation device located proximal to and across the tunnel 522—thereby to retain the graft relative to the fixation device and the bone.

It will be appreciated that by locating the second aperture (e.g. 134) on the second end 114, and by applying tension to the leading length 314 of the suture loop, the device is drawn through the tunnel in an end-on configuration (e.g. as shown in FIG. 4D and FIG. 5A). Typically the second aperture is located on the second end of the device proximal to a central longitudinal axis. Travel of the device through the bone tunnel is substantial parallel to the central longitudinal axis. It will be further appreciated that this preferred trajectory can be enhanced by locating the first aperture (e.g. 132) on the second end of the device proximal to a central longitudinal axis.

It will be appreciated that reference to a suture loop represents a preferred element, and can alternatively comprise any strand element or filament element being suitable for medical procedures and having sufficient length and strength to draw the device in use through a bone tunnel.

Figure 6:
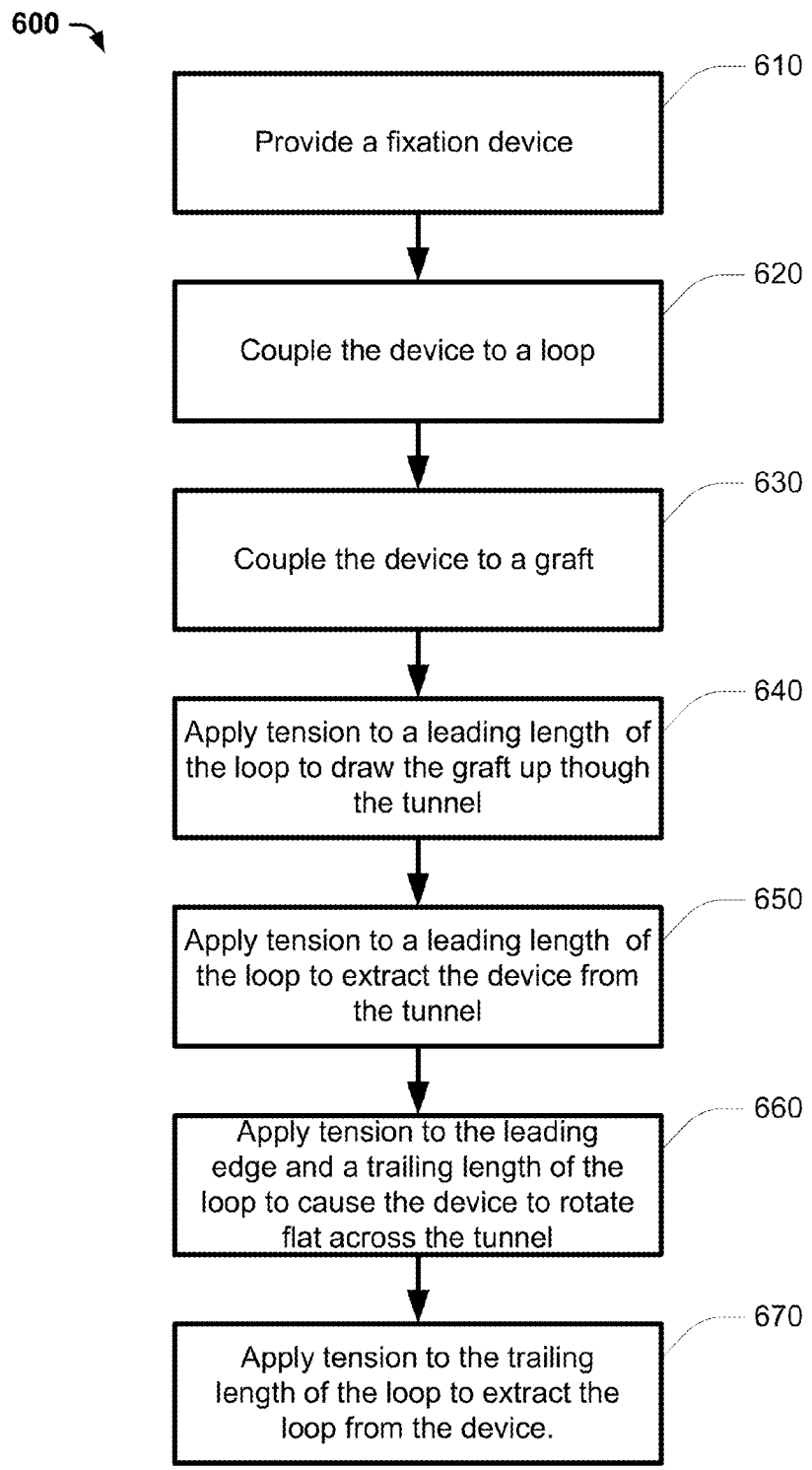
FIG. 6 shows a flowchart for an embodiment method of using a fixation device according to the invention.
Figure 7:
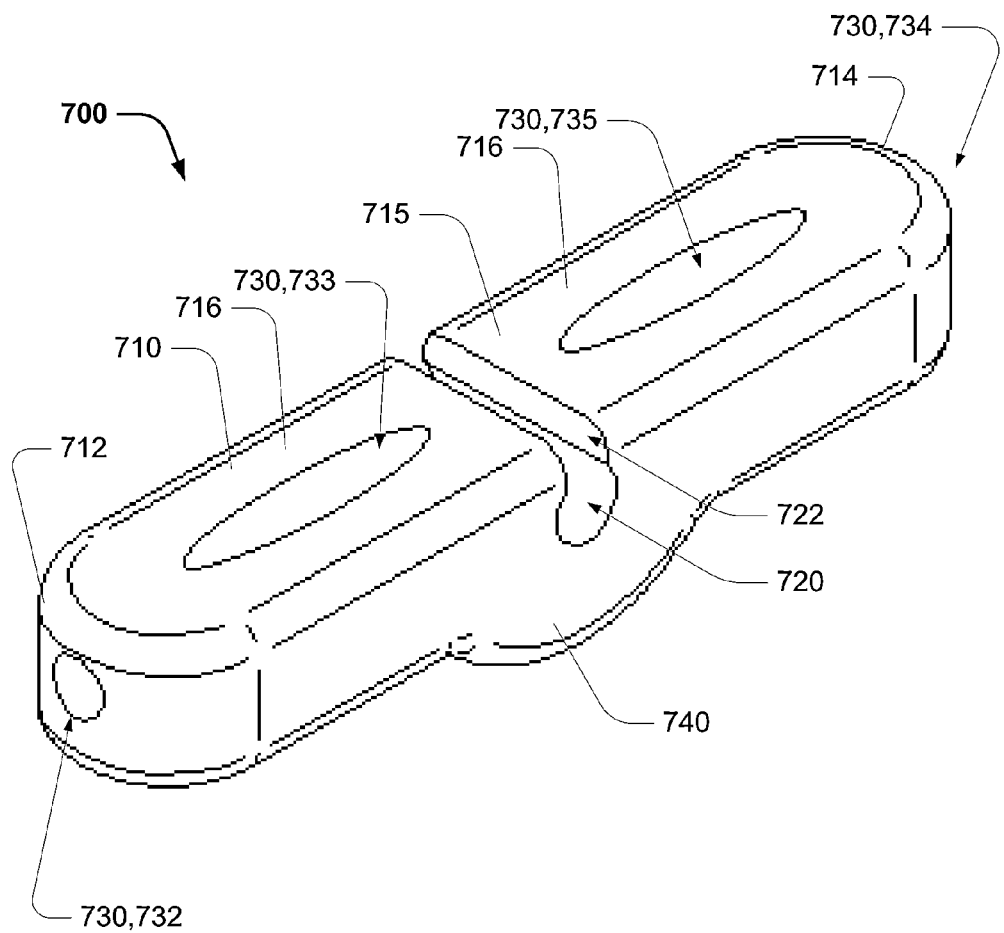
FIG. 7 is a perspective view of an embodiment fixation device according to the invention.

An embodiment method 600, depicted in FIG. 6, is taught for using a fixation device 100 for drawing a graft 330 through a first tunnel (e.g. 522) defined in a first bone (e.g. 520). The method comprising the steps of:
- STEP 610: providing a fixation device 100;
- STEP 620: coupling the fixation device 100 to a loop (for example a loop of suture material 310) having a stop 316 abutting a first end of the fixation device;
- STEP 630: coupling the fixation device to a first end of the graft 330, for example using a graft retainer element 320;
- STEP 640: applying tension to a leading length 314 of the loop to cause the fixation device to draw the graft up through the tunnel—as shown in FIG. 5A;
- STEP 650: applying tension to a leading length 314 of the loop to cause the fixation device to exit the tunnel 522—as shown in FIG. 5B;
- STEP 660: applying tension to the leading edge 314 and a trailing length 312 of the loop to cause the fixation device 100 to rotate flat across the tunnel 522—as shown in FIG. 5C, FIG. 5D and FIG. 5E; and
- STEP 670: applying tension to the trailing length 312 of the loop to thereby extract the loop 310 from the fixation device 100, as shown in FIG. 5F.

A suture is used pulls the device up the tunnel using a knot or expansion at abutting the device. Once the graft is in place the surgeon can keep tension on the suture and rotate/flip the device so it is sitting transversely across a bone aperture. The suture can then be removed by pulling it in the opposite direction.

It will be appreciated by those skilled in the art that other embodied may have many other forms.

Referring to FIG. 7 and FIG. 8A through FIG. 8C, by way of example only, an embodiment fixation device can have the form 700. In this embodiment, the fixation device 700, comprises:
- an elongate body 710 having a first end 712 and a second end 714;
- a transverse passage 720 for retaining a graft retainer element (not shown);
- a longitudinal through passage 730 having a first aperture 732 located in the first end, and a second aperture 734 in the second end.

The first aperture 732 and second aperture 734 defines respective ends of the transverse passage 730 that is not fully enclosed. Typically, the first aperture and the second aperture can be located proximal to the centre of the respective first end and second end.

By way of example only, the longitudinal through passage 730 extends from the first aperture 732 to a first intermediate aperture 733 proximal to the transverse passage 720, and from a second intermediate aperture 735 proximal to the transverse passage 720 to the second aperture 734. In this embodiment, the longitudinal through passage exits at the first intermediate aperture 733 and the second intermediate aperture 733 located on the upper surface 716 of the device.

Figure 8A:
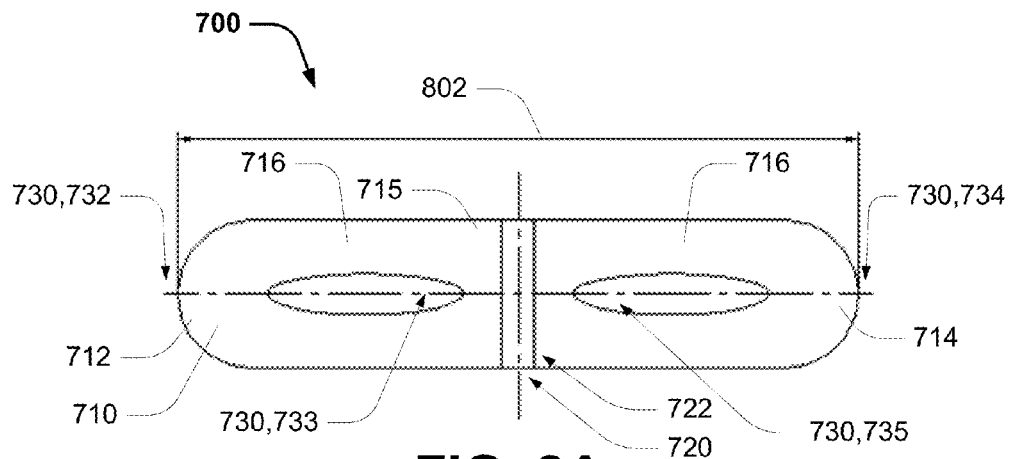
FIG. 8A is a side view of the device of FIG. 7.
Figure 8B:
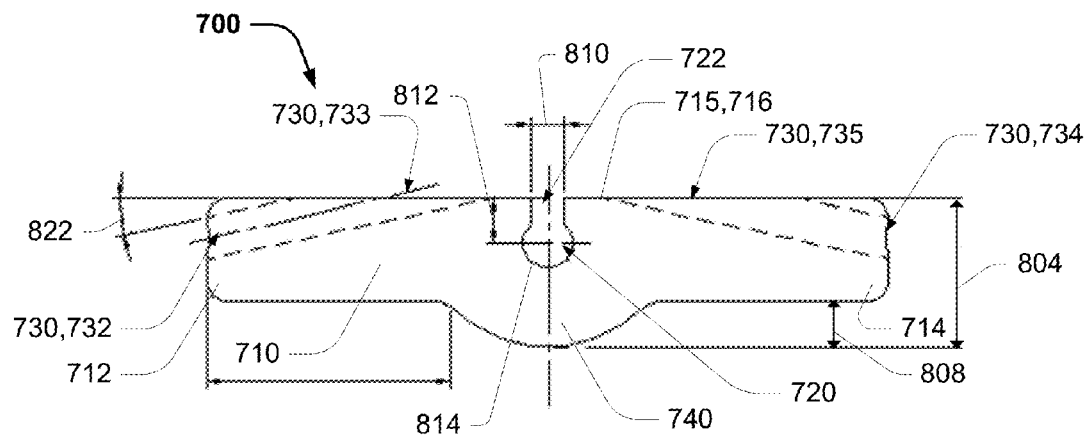
FIG. 8B is a plan view of the device of FIG. 7.

As best shown in FIG. 8B, the longitudinal through passage 730 is defined by a first passage segment 736 and a second passage segment 738, wherein the first passage segment is a substantially straight inwardly-upwardly through-passage extending from the first end 712, and wherein the second passage segment is a substantially straight inwardly-upwardly through-passage extending from the second end 714.

It will be appreciated that, the longitudinal through passage can be defined in a plurality of configurations wherein the passage comprises a first aperture 732 and a second aperture 734 defined proximal to respective ends of the device. For example, in an embodiment, the longitudinal through passage can be axially directed.

In this example, the transverse passage 722 is necked down to resist release of an inserted graft retainer element (not shown).

Figure 8C:
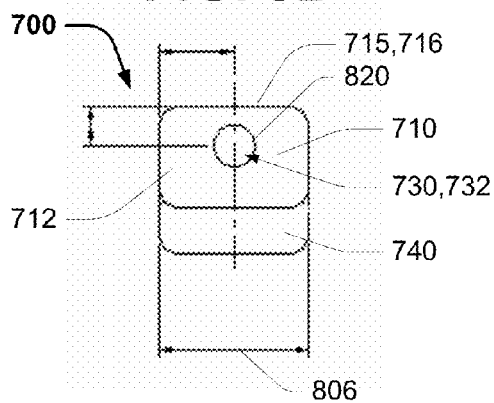
FIG. 8C is an end view of the device of FIG. 7.
Figure 9:
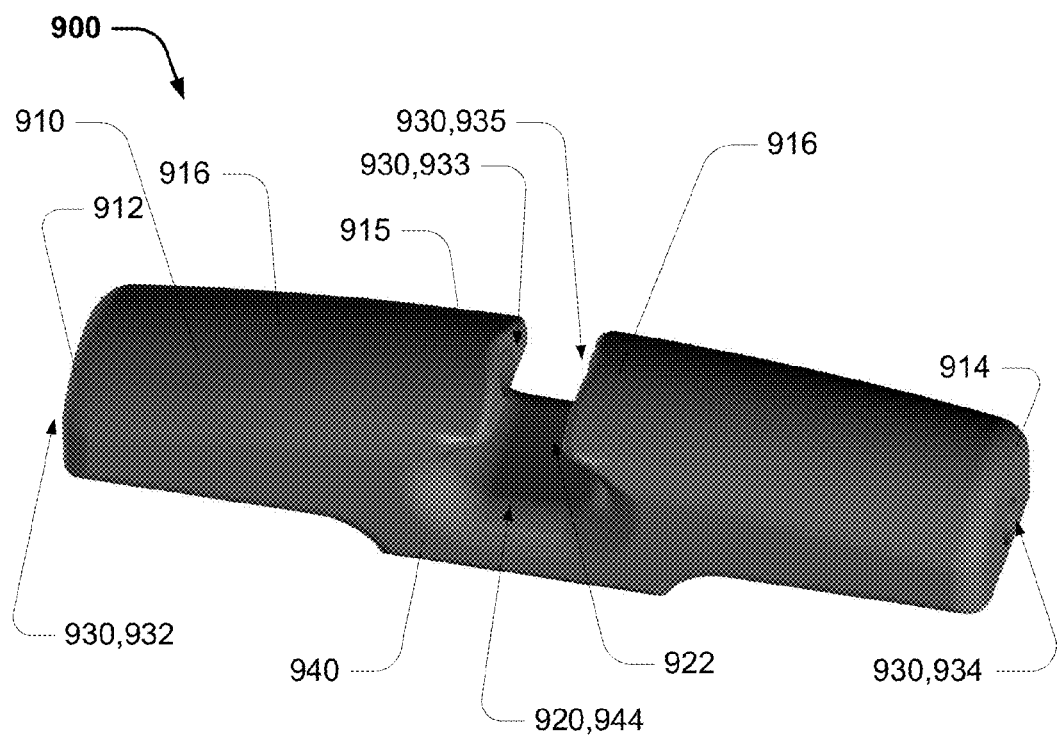
FIG. 9 is a perspective view of an embodiment fixation device according to the invention.
Figure 10A:
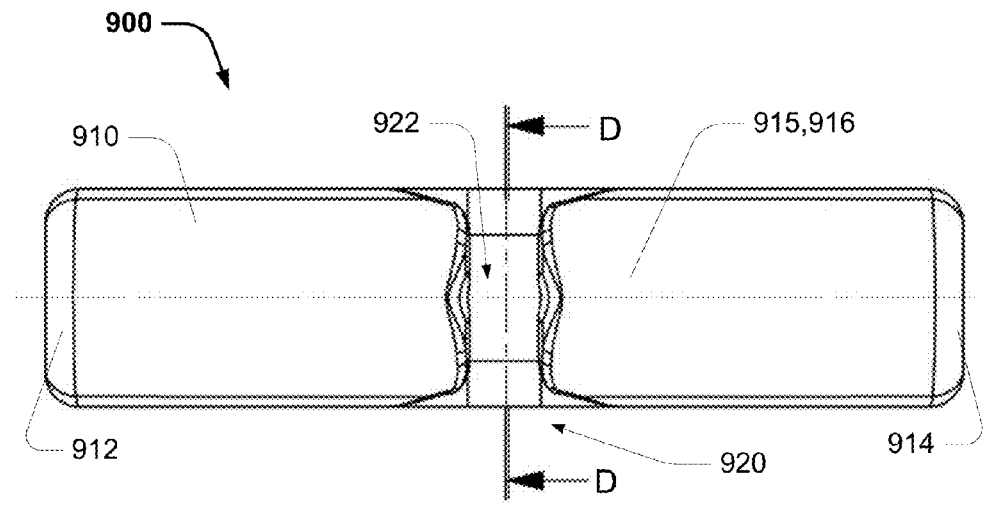
FIG. 10A is a plan view of the device of FIG. 9.
Figure 10B:
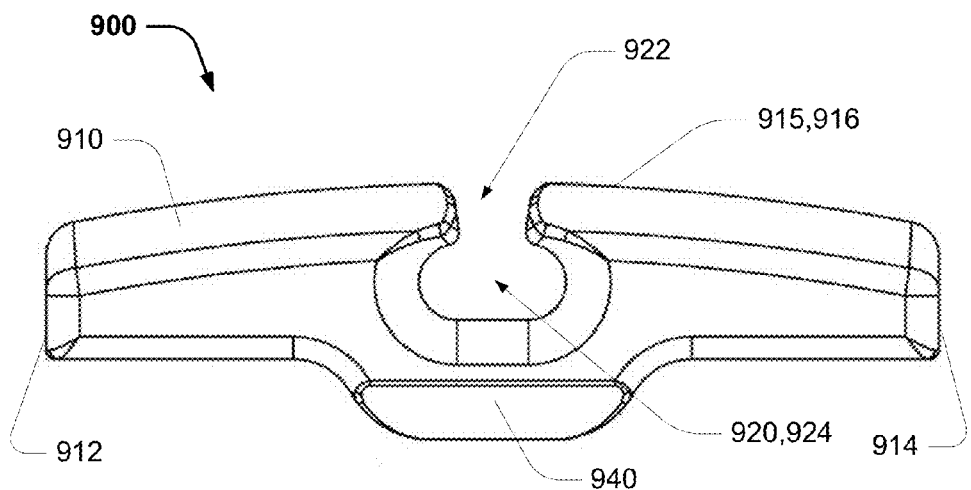
FIG. 10B is a side view of the device of FIG. 9.

Referring to FIG. 8A through FIG. 8C, the fixation device 700 can have:
- an overall length 802 of about 20 mm;
- an overall height 804 of about 5 mm;
- an overall width 206 of about 5 mm;
- a lower protruding portion height 208 of about 1.5 mm;
- a transverse passage having a necked slot width 810 of about 1 mm; a depth 812 of about 1.5 mm; wherein a lower portion of the passage having a diameter 814 of about 1.6 mm;
- a longitudinal through passage having nominal bore diameter 820 of about 1.2 mm, a first passage segment and a second passage segment each inclined 822 at about 12 degrees.

In this example embodiment, in plan view (e.g. FIG. 8A) the body 710 is rectangular having fully rounded edges.

Referring to FIG. 9 and FIG. 10A through FIG. 10E, by way of example only, an embodiment fixation device can have the form 900. In this embodiment, the fixation device 900, comprises:
- an elongate body 910 having a first end 912 and a second end 914;
- a transverse passage 920 for retaining a graft retainer element (not shown);
- a longitudinal through passage 930 having a first aperture 932 located in the first end, and a second aperture 934 in the second end.

The first aperture 932 and second aperture 934 defines respective ends of the transverse passage 930 that is not fully enclosed. Typically, the first aperture and the second aperture can be located proximal to the centre of the respective first end and second end.

By way of example only, the longitudinal through passage 930 extends from the first aperture 932 to a first intermediate aperture 933 proximal to the transverse passage 920, and from a second intermediate aperture 935 proximal to the transverse passage 920 to the second aperture 934. In this embodiment, the longitudinal through passage exits at the first intermediate aperture 933 and the second intermediate aperture 933 located in cavity defined by the transverse passage 920 of the device.

As best shown in FIG. 10E, the longitudinal through passage 930 is defined by a first passage segment 936 and a second passage segment 938, wherein the first passage segment is a substantially straight inwardly-upwardly through-passage extending from the first end 912, and wherein the second passage segment is a substantially straight inwardly-upwardly through-passage extending from the second end 914. In this embodiment, each passage segment 936, 938 is inwardly-upwardly directed at an angle of 12 to 15 degrees, and having a bore diameter of about 1 mm.

In this example embodiment, the first passage segment and the second passage segment of the longitudinal through passage have an aperture located within the surface defining the transverse passage.

It will be appreciated that, the longitudinal through passage can be defined in a plurality of configurations wherein the passage comprises a first aperture 932 and a second aperture 934 defined proximal to respective ends of the device. For example, in an embodiment, the longitudinal through passage can be axially directed.

In this example, the transverse passage 920 is necked down 922 to define a substantially oval passage 924 for resisting release of an inserted graft retainer element (not shown). It will ne appreciated that the substantially oval profile 924 of the transverse passage 920 enables the graft retainer to move toward one end when the device is drawn end-on though a bone passage.

In this example embodiment, in plan view (e.g. FIG. 8A) the body 910 is rectangular having fully rounded edges, and a convex upper surface. It will be appreciated that the edges and corners of the device are curved to minimise risk of the device cutting or gouging, or becoming caught or snagged during use.

It will be appreciated that the illustrated device can retain a graft located with a bone tunnel. The graft is a ligament or tendon being either a transplant or artificial. The device can be used during surgery (in particular knee surgery) when replacing a tendon or ligament.

It will be further appreciated that by including a the transverse passage that is symmetric and slightly longitudinally extended, for example such that is necked down to define a more oval passage, it reduces the risk that of incorrect orientation (e.g. longitudinal-direction) of the device during use— and which enables the stop (or knot) to be proximal to either end during preliminary configuration of the device.

It will be further appreciated that the device may be sided (i.e. a smaller version), such that during use a smaller tunnel is first drilled through the outer femoral cortex and then a larger tunnel is drilled not all the way through the cortex. This configuration can be (but is not limited to) a substantially similar length to the previously disclosed devices (for example about 12 mm) but having an overall diameter of about 4.5 mm.

Although the invention has been described with reference to specific examples, it will be appreciated by those skilled in the art that the invention may be embodied in many other forms.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

Similarly, it is to be noticed that the term coupled, when used in the claims, should not be interpreted as being limitative to direct connections only. The terms "coupled" and "connected", along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, or that two or more elements are not in direct contact with each other but yet still co-operate or interact with each other.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

As used herein, unless otherwise specified the use of terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader, or with reference to the orientation of the structure during nominal use, as appropriate. Similarly, the terms "inwardly" and "outwardly" generally refer to the orientation of a surface relative to its axis of elongation, or axis of rotation, as appropriate.

Similarly it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

It will be appreciated that an embodiment of the invention can consist essentially of features disclosed herein. Alternatively, an embodiment of the invention can consist of features disclosed herein. The invention illustratively disclosed herein The claims defining the invention are as follows:

1. A fixation device for a graft, the device comprising:
   an elongate body having a first end and a second end;
   a transverse passage for retaining a graft retainer element;
   a first aperture located in the first end, and a second aperture in the second end;
   the first aperture and second aperture defining respective ends of a longitudinal through path; and
   a suture having a stop abutting the first end of the elongate body.

2. The device according to claim 1, wherein the body has a lower protruding portion located below the transverse passage.

3. The device according to claim 2, wherein the lower protruding portion is a transverse smooth bulged portion with a width that extends at least the longitudinal span of the transverse passage.

4. The device according to claim 2, wherein the transverse passage is defined as a channel being open to an upper surface of the device.

5. The device according to claim 4, wherein a lower portion of the channel extends toward the first end.

6. The device according to claim 5, wherein the channel has an hook or 'L' shaped profile.

7. The device according to claim 2, wherein the transverse passage is by a closed through aperture.

8. The device according to claim 5, wherein the body tapers-down toward the second end.

9. The device according to claim 5, wherein the body tapers down from a central region toward both the first end and the second end.

10. The device according to claim 5, the device further including the graft retainer element in the form of a closed loop element located in the transverse passage for retaining the graft with respect to the device.

11. The device according to claim 10, wherein the first aperture and the second aperture are located proximal to the centre of the respective first end and second end; and the longitudinal through path is sized to receive a length of suture.

12. The device according to claim 1, wherein the longitudinal through path is intersected by the transverse passage.

13. The device according to claim 12, wherein the longitudinal through path extends from the first aperture to a first intermediate aperture proximal to the transverse passage, and from a second intermediate aperture proximal to the transverse passage to the second aperture.

14. The device according to claim 13, wherein the longitudinal through path is defined by a first passage segment and a second passage segment, each passage segment being substantially straight inwardly-upwardly through-passages extending from a respective first end and second end.

15. The device according to claim 1, wherein the longitudinal through path is an axially directed through passage.

16. A method of using a fixation device according to claim 1 for drawing a graft through a first tunnel defined in a first bone, the method comprising the steps of:
   (a) providing the fixation device;
   (b) coupling the fixation device to a length of suture having a stop abutting a first end of the fixation device;
   (c) coupling the fixation device to a first end of the graft;
   (d) applying tension to a leading portion of the length of suture to cause the fixation device to draw the graft up through the tunnel;
   (e) applying tension to a leading portion of the length of suture to cause the fixation device to exit the tunnel;
   (f) applying tension to the leading edge and a trailing portion of the length of suture to cause the fixation device to rotate flat across the tunnel; and
   (g) applying tension to the trailing portion of the length of suture to thereby extract the length of suture from the fixation device.

17. The method of claim 16, wherein the step (d) further includes:
   applying tension to a leading portion of the length of the suture to cause the fixation device to draw the graft up through the tunnel, such that the first end of the fixation device is a trailing end as the fixation device is drawn up through the tunnel, with the stop of the suture abutting the trailing end.

18. A fixation device for a graft, the device comprising:
   an elongate body having a first end and a second end;
   a transverse passage for retaining a graft retainer element, the body having a lower protruding portion located below the transverse passage, wherein the lower protruding portion has a width that extends at least the longitudinal span of the transverse passage;
   a first aperture located in the first end, and a second aperture in the second end; and
   the first aperture and second aperture defining respective ends of a longitudinal through path.

19. A fixation device for a graft, the device comprising:
   an elongate body having a first end and a second end;
   a transverse passage for retaining a graft retainer element;
   a first aperture located in the first end, and a second aperture in the second end;
   the first aperture and second aperture defining respective ends of a longitudinal through path;
   a suture extending through the longitudinal through path; and
   a graft retainer element extending through the transverse passage.

20. The fixation device of claim 19, wherein the graft retainer element is a closed loop.

21. A fixation device for a graft, the device including:
   an elongate body having a first end and a second end;
   a transverse passage for retaining a graft retainer element, the elongate body having a lower protruding portion located below the transverse passage, wherein the lower protruding portion has a width that extends at least the longitudinal span of the transverse passage;
   a first aperture located in the first end, and a second aperture in the second end;
   the first aperture and second aperture defining respective ends of a longitudinal through path;
   a suture having a stop abutting the first end of the elongate body, the suture extending through the longitudinal through path; and
   a graft retainer element being separate from the suture and extending through the transverse passage, the graft retainer element formed as a closed loop.

22. A fixation device for a graft, the device comprising:
   an elongate body having a first end and a second end;
   a transverse passage;
   a first aperture located in the first end, and a second aperture located in the second end;
   the first aperture and second aperture defining respective ends of a longitudinal through path;
   a graft retainer element retained within the transverse passage;
   a length of suture threaded through the longitudinal through path having a stop abutting one of the first end or second end of the elongate body; and a lower protruding portion located below the transverse passage and sized to locate the fixation device about a bone tunnel;

wherein the graft retainer element is in the form of a closed loop element.

23. The device of claim 22 wherein the stop in the length of suture is a knot.

24. The device of claim 22 wherein the length of suture having a stop abutting one of the first end or second end of the elongate body is configured to enable a user to draw the device through a bone tunnel.

* * * * *